(12) United States Patent
Grate et al.

(10) Patent No.: US 8,507,606 B2
(45) Date of Patent: Aug. 13, 2013

(54) BIOCOMPOSITE MATERIALS AND METHODS FOR MAKING THE SAME

(75) Inventors: Jay W. Grate, West Richland, WA (US); Jungbae Kim, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 1500 days.

(21) Appl. No.: 11/983,516

(22) Filed: Nov. 9, 2007

(65) Prior Publication Data

US 2011/0236951 A1    Sep. 29, 2011

Related U.S. Application Data

(62) Division of application No. 10/326,201, filed on Dec. 20, 2002, now Pat. No. 7,311,926.

(51) Int. Cl.
*A61K 47/48* (2006.01)
*C08G 63/48* (2006.01)
*C08G 63/91* (2006.01)
*C08L 89/00* (2006.01)

(52) U.S. Cl.
USPC .................................................. 525/54.1

(58) Field of Classification Search
USPC .................................................. 525/54.1
See application file for complete search history.

(56) References Cited

U.S. PATENT DOCUMENTS

| | | | |
|---|---|---|---|
| 3,985,616 A | 10/1976 | Weaver et al. | |
| 4,370,160 A * | 1/1983 | Ziemelis | 504/323 |
| 4,371,612 A | 2/1983 | Matsumoto et al. | |
| 4,665,028 A | 5/1987 | Amotz | |
| 4,727,303 A | 2/1988 | Morse et al. | |
| 5,281,355 A | 1/1994 | Tsaur et al. | |
| 5,281,356 A | 1/1994 | Tsaur et al. | |
| 5,441,660 A | 8/1995 | Tsauer et al. | |
| 5,482,996 A | 1/1996 | Russell et al. | |
| 5,498,421 A | 3/1996 | Grinstaff et al. | |
| 5,665,383 A | 9/1997 | Grinstaff et al. | |
| 5,718,915 A | 2/1998 | Virtanen et al. | |
| 5,719,039 A | 2/1998 | Dordick et al. | |
| 5,817,493 A * | 10/1998 | Reetz et al. | 435/182 |
| 5,914,367 A | 6/1999 | Dordick et al. | |
| 5,916,790 A | 6/1999 | Enevold | |
| 5,922,537 A * | 7/1999 | Ewart et al. | 435/6.11 |
| 6,020,200 A | 2/2000 | Enevold | |

(Continued)

OTHER PUBLICATIONS

Abuchowski et al., "Alteration of Immunological Properties of Bovine Serum Albumin by Covalent Attachment of Polyethylene Glycol," *The Journal of Biological Chemistry* 252(11):3578-3581, 1977.

(Continued)

*Primary Examiner* — Liam Heincer
(74) *Attorney, Agent, or Firm* — Klarquist Sparkman, LLP (57) ABSTRACT

A particle (and a composition that includes a plurality of the particles) that includes at least one polypeptide molecule and at least one polymer covalently bound to the polypeptide molecule so as to form a polymer shell substantially encompassing the polypeptide molecule, wherein the particle does not define a dimension greater than about 1 μm. One example for making the particle includes modifying the polypeptide molecule to provide α, β-ethylenically unsaturated terminal functional groups, mixing the modified polypeptide molecule with a silicon-containing polymerizable compound, and subjecting the resulting mixture to conditions sufficient for polymerizing the polymerizable compound to form the particle.

20 Claims, 3 Drawing Sheets

(56) References Cited

U.S. PATENT DOCUMENTS

| | | | |
|---|---|---|---|
| 6,030,933 A * | 2/2000 | Herbots et al. | 510/392 |
| 6,033,898 A * | 3/2000 | Sarthy et al. | 435/254.21 |
| 6,291,582 B1 | 9/2001 | Dordick et al. | |
| 6,337,089 B1 | 1/2002 | Yoshioka et al. | |
| 6,359,031 B1 * | 3/2002 | Lykke et al. | 523/201 |
| 6,362,276 B1 * | 3/2002 | Harris et al. | 525/54.1 |
| 6,979,530 B2 * | 12/2005 | Yan et al. | 435/4 |
| 7,311,926 B2 * | 12/2007 | Grate et al. | 424/491 |
| 2001/0050217 A1 | 12/2001 | Uehara et al. | |
| 2002/0020931 A1* | 2/2002 | Stowell et al. | 264/4.1 |
| 2002/0182413 A1* | 12/2002 | Kunitake et al. | 428/403 |
| 2003/0171804 A1 | 9/2003 | Krause | |
| 2004/0121018 A1* | 6/2004 | Grate et al. | 424/490 |
| 2010/0137474 A1* | 6/2010 | Goh et al. | 523/205 |
| 2011/0064652 A1* | 3/2011 | Borlak et al. | 424/1.11 |
| 2011/0237747 A1* | 9/2011 | Zhao et al. | 525/54.1 |

OTHER PUBLICATIONS

Avnir et al., "Recent bio-applications of sol-gel materials," *Journal of Materials Chemistry* 16:1013-1030, 2006.
Bailey and Ollis, "Immobilized-Enzyme Technology," *Biochemical Engineering Fundamentals* (2d ed., McGraw-Hill Book Company), pp. 180-189, 1986.
Bode et al., "Crude Aminoacylase From *Aspergillus* sp. Is a Mixture of Hydrolases," *Biotechnol. Bioeng.* 84:710-713, 2003.
Cabriol et al., "Immobilized Hydroxynitrile Lyases for Enantioselective Synthesis of Cyanohydrins: Sol-Gels and Cross-Linked Enzyme Aggregates," *Adv. Synth. Catal.* 348:1645-1654, 2006.
Cao et al., "Cross-Linked Enzyme Aggregates: A Simple and Effective Method for the Immobilization of Penicillin Acylase," *Organic Letters* 2(10):1361-1364, 2000.
Cao et al., "Cross-linked aggregates of penicillin acylase: robust catalysts for the synthesis of β-lactam antibiotics," *Journal of Molecular Catalysis* 11:665-670, 2001.
Cao et al., "Immobilised enzymes: carrier-bound or carrier-free?," *Current Opinion in Biotechnology* 14:387-394, 2003.
Chmura et al., "Cross-Linked Aggregates of the Hydroxynitrile Lyase from *Manihot esculenta*: Highly Active and Robust Biocatalysts," *Adv. Synth. Catal.* 348:1655-1661, 2006.
Ebsworth, "Silicon Bound to Elements of Group VI," *Volatile Silicon Compounds* (Pergamon Press) p. 137, 1963.
Fischback et al., "Miniature Biofuel Cells with Improved Stability Under Continuous Operation," *Electroanalysis* 18(19-20):2016-2022, 2006.
Greene and Wuts, "Protection for the Carboxyl Group," *Protective Groups in Organic Synthesis* (3d ed., John Wiley & Sons, Inc.), pp. 428-429, 1999.
Hobbs et al., "Continuous kinetic resolution catalysed by cross-linked enzyme aggregates, 'CLEAs', in Supercritical $CO_2$," *Green Chem.* 8:816-821, 2006.
Ito et al., "Catalytic Peptide Synthesis by Trypsin Modified with Polystyrene in Chloroform," *Biotechnol. Prog.* 9(2):128-130, 1993.
Jain et al., "Nanometer Silica Particles Encapsulating Active Compounds: A Novel Ceramic Drug Carrier," *J. Am. Chem. Soc.* 120(43):11092-11095, 1998.
Kim et al., "Protease-Containing Silicates as Active Antifouling Materials," *Biotechnol. Prog.* 18(3):551-555, 2002.
Kim et al., "Preparation of biocatalytic nanofibres with high active and stability via enzyme aggregate coating on polymer nanofibres," *Nanotechnology* 16:S382-388, 2005.
Livages et al., "Enzymes and Cells Confined in Silica Nanopores," www.bichat.inserm.fr/equipes/Emi0339/PDFexhaustlisteOB/2001_MRSSP_24.pdf (downloaded Jun. 7, 2006).
López-Serrano et al., "Cross-linked enzyme aggregates with enhanced activity: application to lipases," *Biotechnology Letters* 24:1379-1383, 2002.

Marinakos et al., "Encapsulation, Permeability and Cellular Uptake Characteristics of Hollow Nanometer-Sized Conductive Polymer Capsules," *J. Phys. Chem. B* 105(37):8872-8876, 2001.
Mateo et al., "A New, Mild Cross-linking Methodology to Prepare Cross-Linked Enzyme Aggregates," *Biotechnology and Bioengineering* 86(3):273-276, 2004.
Mateo et al., "Stabilisation of oxygen-labile nitrilases via co-aggregation with poly(ethyleneimine)," *Journal of Molecular Catalysis B: Enzymatic* 38:154-157, 2006.
Mateo et al., "Synthesis of enantiomerically pure (S)-mandelic acid using an oxynitrilase-nitrilase bienzymatic cascade: a nitrilase surprisingly shows nitrile hydratase activity," *Tetrahedron: Asymmetry* 17:320-323, 2006.
Novick et al., "Preparation of Active and Stable Biocatalytic Hydrogels for Use in Selective Transformations," *Chem. Mater.* 10(4):955-958, 1998.
Novick et al., "Investigating the Effects of Polymer Chemistry on Activity of Biocatalytic Plastic Materials," *Biotechnology and Bioengineering* 68(6):665-671,2000.
Novick et al., "Protein-containing hydrophobic coatings and films," *Biomaterials* 23:441-448, 2002.
Paradkar et al., "Aqueous-like Activity of α-Chymotrypsin Dissolved in Nearly Anhydrous Organic Solvents," *J. Am. Chem. Soc.* 116(10:5009-5010, 1994.
Pina et al., "The Activity of Peg-Modified Chymotrypsin in Aqueous and Organic Media," *Biotechnology Techniques* 3(5):333-338, 1989.
Rochow, "The Simple Covalent Compounds of Silicon," *An Introduction to the Chemistry of Silicones* (2d ed., John Wiley & Sons, Inc.), pp. 16, 1946 and 1951.
Schoevaart et al., "Preparation, Optimization, and Structures of Cross-Linked Enzyme Aggregates (CLEAs)," *Biotechnology and Bioengineering* 87(6):754-762, 2004.
Sheldon et al., "CLEAS: An effective technique for enzyme immobilization," *Specialty Chemicals Magazine*, pp. 40-42, Jul./Aug. 2003.
Sheldon et al., "Cross-linked enzyme aggregates (CLEAs): A novel and versatile method for enzyme immobilization (a review)," *Biocatalysis and Biotransformation* 23(3/4):141-147, 2005.
Sheldon et al., "Cross-linked enzyme aggregates (CLEAs)," *Methods in Biotechnology 22. Immobilization of enzymes an cells* ($2^{nd}$ed.), Humana Press, Totowa, NJ, pp. 31-45, 2006.
Sheldon, "Immobilization of Enzymes as Cross-Linked Enzyme Aggregates: A Simple Method for Improving Performance," *Biocatalysis in the Pharmaceutical and Biotechnology Industries*, CRC Press, Taylor & Francis Group, Boca Raton, FL, pp. 351-362, 2006.
Sheldon et al., "Use of Cross-Linked Enzyme Aggregates (CLEAs) for performing biotransformations," *Chemistry Today* 25(1):62-67, 2007.
van Langen et al., "Penicillin Acylase Catalysed Synthesis of Ampicillin in Hydrophilic Organic Solvents," *Adv. Synth. Catal.*, 345:797-807, 2003.
van Langen et al., "Cross-Linked Aggregates of (R)-Oxynitrilase: A Stable, Recyclable Biocatalyst for Enantioselective Hydrocyanation," *Organic Letters* 7(2):327-329, 2005.
Wang et al., "Biocatalytic plastics as active and stable materials for biotransformations," *Nature Biotechnology* 15:789-793, 1997.
Yang et al., "Activity and Stability of Enzymes Incorporated into Acrylic Polymers," *J. Am. Chem. Soc.* 117(17):4843-4850, 1995.
"An Overview of the Organic-Inorganic Mesoporous Silica Materials and their Application as Host Matrix for Protein Molecules," Chapter 1, dspace.library.drexel.edy/retrieve/1026/ch1.pdf (downloaded Jun. 7, 2006).
Definition of Macroporous Polymer from *Pure Appl. Chem.* 76(4):889-906, 2004.
"Science: Uncovering and Discovering, Enzymes Immobilized," http://technical.scienceboard.net/archives/2005/10/14/24 (downloaded Jun. 7, 2006).

* cited by examiner

BIOCOMPOSITE MATERIALS AND METHODS FOR MAKING THE SAME

CROSS REFERENCE TO RELATED APPLICATIONS

This is a divisional of U.S. patent application Ser. No. 10/326,201, filed Dec. 20, 2002, now U.S. Pat. No. 7,311,926, which is incorporated herein in its entirety.

STATEMENT OF GOVERNMENT SUPPORT

This invention was made with United States Government support under Contract DE-AC06-76RL01830 awarded by the U.S. Department of Energy. The United States Government has certain rights in the invention.

BACKGROUND

Polypeptides or proteins, such as enzymes, are useful nanoscale bio-macromolecules, but the short lifetime of these nanobiological systems presently limits their usefulness. Enzyme immobilization is one of the most important methodologies that can provide enzyme stabilization. However, previously developed stable enzyme systems generally provide poor enzyme activity. Conversely, previously developed active enzyme systems generally display poor enzyme stability. Despite significant efforts, the development of enzyme systems that are both active and stable continues to be a great challenge.

BRIEF DESCRIPTION OF THE DRAWINGS

Certain examples are described below with reference to the following figures.

DETAILED DESCRIPTION OF SEVERAL EXAMPLES

For ease of understanding, the following terms used herein are described below in more detail:

"Nanoparticle" denotes a discrete particle that does not have any dimension greater than about 1 μm.

"Polypeptide" refers to a polymer in which the monomers are amino acid residues that are joined together through peptide bonds, and encompasses any amino acid sequence, including modified sequences such as glycoproteins. "Proteins" encompasses proteins, fragments thereof, and conjugated proteins. The term "polypeptide" or "protein" is specifically intended to cover naturally occurring proteins, as well as those that are recombinantly or synthetically produced. Functional fragments of a polypeptide or protein refers to all fragments of a polypeptide or protein that retain an activity, or a measurable portion of an activity, of the polypeptide or protein from which the fragment is derived. Fragments, for example, can vary in size from a polypeptide fragment as small as an epitope capable of binding an antibody molecule to a large polypeptide capable of participating in the characteristic induction or programming of phenotypic changes within a cell.

"Silyl" refers to a functional group having a structure represented by —$SiH_3$.

"Substituted silyl" refers to a functional group having a structure wherein at least one of the hydrogen molecules of a silyl group have been replaced with another functional group such as an alkoxy or hydroxy group.

The above term descriptions are provided solely to aid the reader, and should not be construed to have a scope less than that understood by a person of ordinary skill in the art or as limiting the scope of the appended claims.

Disclosed herein are unique biocomposite materials that generally include at least one polypeptide or protein molecule partially or substantially encapsulated within an organic/inorganic shell. The shell typically is sufficiently porous so that the shell does not deleteriously interfere with the bioactivity of the protein. For example, the shell may be sufficiently porous to allow the encapsulated protein to digest substrates having molecular weights up to about 70 kilodaltons. The ability to permit digestion of relatively large substrates can substantially increase the range of substrates that can be used with the biocomposite materials. Another characteristic of the biocomposite materials is that they generally exhibit a minimal, if any, mass-transfer limitation between the protein molecule and a substrate. For example, the biocomposite materials may have an observed effectiveness factor (OEF or η) of at least about 0.7, and more particularly about 0.9. The OEF, defined by the ratio of reaction rates with and without the shell, may be calculated by dividing the apparent binding constant ($K_m^{app}$) of the free protein (i.e., a protein molecule that is not bound to the polymer shell) by the $K_m^{app}$ of the biocomposite. The effective porosity of the shell may be adjusted, for example, by controlling the extent of chain-extension polymerization and polymer crosslinking as described in more detail below.

On the other hand, the shell may be sufficiently bound to the protein to form an effective thermodynamic barrier for increasing the stability of the polypeptide's or protein's bioactivity. For example, if the encapsulated protein is an enzyme, substrates for the enzyme may diffuse through the shell but the shell contributes to increasing the activation energy required for transition of the protein from the native form to the denatured form. The inorganic domain of the shell further provides additional hardness and structural integrity to the biocomposite, and thus enables the biocomposite to better withstand structural stress and frictional forces during use of the biocomposite. Consequently, the biocomposite dramatically stabilizes the enzyme activity.

The biocomposite materials typically are in the form of solid nanoparticles. The nanoparticle may assume a variety of geometrical shapes such as generally spherical, oval, tubular, or asymmetrical. The shape of nanoparticles that contain only a single protein or polypeptide molecule in the nanoparticle core generally will be similar to the shape of the native or free protein or polypeptide molecule. The shell typically has an average thickness of only about 0.2 to about 200 nm, more particularly about 1 to about 50 nm. In the case of nanoparticles that contain only a single protein or polypeptide molecule, the shell thickness may be more particularly about 0.2 to about 10 nm, especially about 1 to about 5 nm. The shell forms a distinct or discrete layer at the surface of the polypeptide or protein molecule, which may be visually discernible under appropriate magnification for nanoparticles that contain only a single protein or polypeptide molecule (see FIGS. 3 and 4 described below). Consequently, the nanoparticles generally do not have any dimensions that are greater than about 1 μm. The nanoparticles often do not have a dimension greater than about 200 nm, more particularly about 100 nm, and even more particularly not greater than about 50 nm. There is no critical limitation on the minimum size of the nanoparticle, but the nanoparticle typically defines a dimension of at least about 2 nm.

The biocomposite material can be formed from at least one polypeptide or protein or a mixture of different types of polypeptides or proteins. The protein may be, for example, an enzyme, a hormone, a toxin, an antibody, an antigen, a lectin, a structural protein, a signal protein, a transport protein, a receptor, a blood factor, or a mixture thereof. According to particular examples, the protein is an enzyme such as proteases (e.g., chymotrypsin, trypsin, subtilisin, and papain), lipases, peroxidases (e.g., horseradish peroxidase, soybean peroxidase, chloro peroxidase, and manganese peroxidase), tyrosinase, laccase, cellulase, xylanase, lactase, sucrase, organophosphohydrolase, cholinesterase, glucose oxidase, alcohol dehydrogenase, glucose dehydrogenase, hydrogenase, and glucose isomerase. In a specific variant, the nanoparticle biocomposite includes a single protein molecule encompassed by the shell. However, the core may be a protein construct that includes more than one protein molecule. For example, several polypeptide or protein molecules may be crosslinked together by contacting the polypeptide or protein molecules with glutaraldehyde, toluene diisocyanate, or diphenylmethane diisocyanate. The polypeptide or protein may be a fusion protein. As used herein, "protein molecule core" encompasses such plural-molecule constructs.

Specific examples of nanoparticle cores that include more than one polypeptide or protein molecules are cores that could perform sequential transformations on a substrate by two or more enzymatic reactions. Thus, the nanoparticle could be a bioreactor executing more than one transformation to convert a molecule into a desired product. For example, the nanoparticle bioreactor could include appropriate polypeptide or protein molecules to replicate a metabolic pathway within living tissue. The close proximity of the core proteins that can be obtained with the nanoparticles will promote the sequential reactions.

One illustrative plural-molecule core is a system that includes a glucose oxidase molecule and a peroxidase molecule in the core. The glucose oxidase can convert glucose to glucuronic acid and hydrogen peroxide. The hydrogen peroxide can be used for the peroxidase reaction with a reporter fluorescence molecule (for glucose biosensing) or a phenol (for bioremediation of phenol). Another illustrative example is a system that includes glucose dehydrogenase and hydrogenase in the core. The glucose dehydrogenase can convert glucose into glucuronic acid, and reduce nicotinamide adenine dinucleotide phosphate (NADP) to reduced nicotinamide adenine dinucleotide phosphate (NADPH). The NADPH can be used for the hydrogenase reaction to produce hydrogen. A further illustrative example is a system that includes invertase, glucose dehydrogenase, and hydrogenase in the core. The invertase cleaves sucrose to glucose and fructose, and glucose can be used for the production of hydrogen via catalysis with glucose dehydronase and hydrogenase as described above. Glucose isomerase may be added for converting fructose to glucose. Certain enzymes can also be included in the particle core construct for producing glucose from target molecules in agricultural biomass. For instance, cellulase, xylanase, and lactase (β-glucosidase) can be employed for hydrolyzing cellulose, xylan, and lactose, respectively, into their constituent sugars.

The nanoparticle biocomposites can be provided in a variety of useful forms or media. For example, a multitude of individual nanoparticles could be dried resulting in a powder composition. The nanoparticles may be dispersed, suspended or dissolved in a liquid media. The nanoparticles may be dissolved in water such as an aqueous buffer or an organic solvent (provided the polymer shell has been functionalized with appropriate hydrophobic groups). The versatility of the solubility of the nanoparticles is advantageous since many enzymatic synthetic reactions can occur in aqueous or organic solvents.

The composite shell usually is chemically bound to the polypeptide or protein. The chemical bond may be any type of bond, but covalent bonding is especially useful. The chemical bond is primarily formed with functional groups or moieties that are present on or near the surface of the protein as described below in more detail.

A feature of the polymer shell is that there is substantially no crosslinking between each individual polymer-encapsulated protein molecule core. Each nanoparticle is a discrete particle having a protein construct core substantially encapsulated only by an individual polymer shell. In other words, the crosslinking occurs only between polymers chains covalently attached to the same protein molecule core. There is substantially no inter-protein crosslinking between a first polymer chain covalently attached to a first protein molecule and a second polymer chain covalently attached to a second protein molecule that is spaced apart from the first protein molecule. According to the synthesis disclosed herein, the crosslinking may be limited to prevent the formation of a polymer network or matrix that encapsulates a plurality of spaced-apart protein molecules. Examples of such inter-protein crosslinked polymer networks are shown, for instance, in U.S. Pat. No. 6,291,582 (FIG. 1) and Norvick et al., "Investigating the Effects of Polymer Chemistry on Activity of Biocatalytic Plastic Materials", *Biotech. and Bioeng.*, 68, 665-671 (FIG. 1).

The shell material may include at least one inorganic moiety. One example is a silicon-containing moiety or functional group such as a silane or a siloxane functional group. In an illustrative example the shell may be a polysiloxane such as a polyorganosiloxane. The polysiloxane is covalently bound to the protein via linking groups. One example of linking groups is residues produced from ethylenically-unsaturated carbon functional groups, particularly vinyl groups, that have undergone addition polymerization.

Synthesis

According to one illustrative synthesis approach, the process begins at the surface of the polypeptide or protein molecule, with covalent reactions to anchor, grow, and crosslink an individual polymer composite shell around each protein molecule. The process may involve two-phase reaction and extraction systems, as well as selective filtering or separation to isolate the biocomposite nanoparticles. Examples of particular process steps are described below in more detail.

A polypeptide or protein molecule typically is initially contacted with a modifier compound so that the free amino, carboxyl, and/or sulfide groups of the protein are modified to include (a) a reactive group that is polymerizable with at least one second compound, or (b) a reactive group that by itself can undergo subsequent polymerization. The option (a) approach will be described first.

The second compound in the option (a) approach may be referred to throughout this application as the "shell-forming compound." The polymerizable reactive groups, along with reactive groups of the second compound, provide the covalent bonding of the organic/inorganic polymer shell to the individual protein molecule. In addition, the modifying reactive groups can assist in solubilization of the protein in an organic solvent.

The modifier compound includes a functional group that is reactive with free amino groups, carboxyl, and/or thiol present in the protein molecule to provide the desired functionalization of the protein molecule. Typical amino-reactive groups include carboxy groups (—COOH); carboxylate ionic groups (—COOX, wherein X is selected from a halogen such as Cl or Br); carbonyl halide groups (—COX, wherein X is a halogen selected from Cl, Br, F or I); succinyl groups (—OCCH$_2$CH$_2$CO—); epoxy groups; and isocyanato groups. Typical carboxyl-reactive groups include amino groups such as a diimide linker (e.g., 1-ethyl-3-(3-dimethylaminopropyl) carbodiimide hydrochloride).

The group of the modifier compound that is reactive with the shell-forming compound may be an α, β-ethylenically unsaturated terminal functional group such as, for example, a vinyl group or an allyl group. According to a specific example, a vinyl group functionality is grafted onto the surface of enzymes by covalently modifying substantially most of the amino groups on the enzyme surface. Suitable modifier compounds include vinyl compounds such as (meth)acrylic acid, (meth)acrylate, substituted (meth)acrylate, and acryloyl chloride. Such vinyl compounds should also include amino, carboxyl, and/or sulfide-reactive groups for forming a covalent bond to the polypeptide or protein molecule as described above.

Further examples of possible modifier compounds include polyethylene glycol compounds. Polyethylene glycols can include terminal functional groups such as amino, carboxyl, hydroxy, thiol, and acryl groups that can be reacted with the polypeptide or protein molecule in an aqueous buffer. Thus, the polyethylene glycol chain can be covalently bonded to the surface of the polypeptide or protein molecule. Acrylated polyethylene glycol and similar compounds described, for example, in U.S. Pat. No. 5,482,996 and Yang et al., "Activity and Stability of Enzymes Incorporated into Acrylic Polymers", *J. Am. Chem. Soc.* 1995, 117, 4843-4850. The polyethylene glycol can also include a pendant functional group that is reactive with a shell-forming compound. Such functional groups include amino, carboxyl, and/or hydroxyl groups. Crosslinking of these functional groups with a shell-forming compound is described in more detail below.

The modifier compound may be mixed with the polypeptide or protein under any conditions sufficient for achieving the desired terminal group modification. For example, the protein may be dissolved in an aqueous solution such as a buffered solution. The modifier compound then is mixed into the protein-containing buffer and allowed to react with the protein molecules. In the case of nanoparticle core constructs that include more than one protein molecule, the individual protein molecules may be each initially surface-modified and then linked together to form the core construct. The amount of modifier typically is sufficient to modify a substantial amount, if not all, of the free amino, carboxyl, and/or sulfide groups. The temperature of the reaction mixture is controlled so as to avoid damaging the bioactivity of the protein molecules. One example of a possible temperature range is from about 0° C. to about 4° C. The buffer is used to maintain the pH of the aqueous solution at the desired level. For example, if an anionic or cationic surfactant is used for solubilizing the protein in an organic solvent, then the pH of the aqueous solution is adjusted accordingly to provide the protein with an appropriate negative or positive net surface charge. Alternatively, if a certain protein has an optimal pH range for bioactivity and stability, then a suitable anionic or cationic surfactant can be selected depending upon the net surface charge of the protein. For example, protein molecules will be positively charged if the pH value of the buffer solution is lower than the protein's pI, and will be negatively charged if the pH value is higher than the protein's pI. Specific illustrations of this approach include α-chymotrypsin which has a pI of 8.8 and an optimal pH of 7.8 for bioactivity. Thus, the net surface charge of α-chymotrypsin at a pH of 7.8 is positive, meaning that an anionic surfactant should be employed. Similarly, trypsin has a pI of 10.2 and optimal bioactivity pH of 8, and thus an anionic surfactant also would be utilized. Tyrosinase, on the other hand, has a pI of 4.7 and an optimal bioactivity pH of 6.5. Accordingly, a cationic surfactant would be used with tyrosinase.

The α, β-ethylenically unsaturated-modified proteins typically are insoluble or display limited solubility in organic solvents. On the other hand, many polymerizable compounds useful for forming the covalently-bound shell are soluble in organic solvents, but not in water. Thus, an optional step in the synthesis disclosed herein involves solubilizing the modified protein in an organic solvent. There are at least two solubilizing techniques that may be suitable. One technique is described in more detail below and involves the use of surfactants. The other technique involves modifying the protein surface with hydrophobic functionality such as acrylated polyethylene glycol (see U.S. Pat. No. 5,482,996 and Yang et al., "Activity and Stability of Enzymes Incorporated into Acrylic Polymers", *J. Am. Chem. Soc.* 1995, 117, 4843-4850). Alternatively, certain useful polymerizable compounds may be water-soluble as described in more detail below. In this alternative scenario, solubilizing of the modified protein in an organic solvent may be avoided, and synthesis may proceed directly to polymerization with the shell-forming compound in an aqueous media.

If the optional protein solubilizing step is employed, one approach involves utilizing a surfactant. In particular, a two-phase system is provided wherein a first phase includes an aqueous solution of the modified protein, and the second phase includes a surfactant dissolved in an organic solvent. The two-phase system is mixed together and forms a protein-surfactant complex. A substantial portion, if not all, of the protein-surfactant complex is extracted into the organic phase.

If an anionic or cationic surfactant is employed, the protein-surfactant complex may be formed by generating a modified protein that has a net surface charge that is opposite the charge of the selected surfactant. Illustrative anionic surfactants include fatty alcohol sulfates, including sodium, potassium, ammonium or triethaniolamine salts of saturated or unsaturated $C_{10}$ to $C_{18}$ hydrocarbons such as sodium dodecyl sulfate (SDS), sodium tetradecyl sulfate, sodium heptadecyl sulfate, and sodium lauryl sulfate (SLS); sodium 2-ethylhexyl sulfate; ethoxylated fatty alcohol sulfates, including alkyl ether sulfates such as sodium lauryl ether sulfate (SLES); sarconisate; alkyl glyceryl ether sulfonate; alpha sulpho fatty acids and esters; fatty acid esters of isethionic acid; acyl (fatty) N-methyltaurides; dialkylsulfo succinate esters including $C_8$, $C_{10}$ and $C_{12}$ forms thereof such as bis(2-ethylhexyl) sodium sulfosuccinate (AOT); N-acylated amino acids, such as sodium N-lauroyl sarconisate or gluconate;

sodium coconut monoglyceride sulfonate; alkyl phosphates such as (2-ethylhexyl) phosphate; and tauroglycocholate. Illustrative cationic surfactants include compounds containing quaternary ammonium hydrophilic moieties in the molecule which are positively charged, such as quaternary ammonium salts or bases that include alkyl groups containing 1-30 carbon atoms, or alkyl groups derived from tallow, coconut oil, or soy; hydroxide; and or halogen. Dialkyl dimethyl ammonium salts and monoalkyl trimethyl ammonium salts may be used. Representative quaternary ammonium salts and hydroxides include dodecyltrimethyl ammonium chloride/lauryltrimethyl ammonium chloride (LTAC), cetyltrimethyl ammonium chloride (CTAC), didodecyldimethyl ammonium bromide, dihexadecyldimethyl ammonium chloride, dihexadecyldimethyl ammonium bromide, dioctadecyldimethyl ammonium chloride, dieicosyldimethyl ammonium chloride, didocosyldimethyl ammonium chloride, dicoconutdimethyl ammonium chloride, ditallowedimethyl ammonium chloride, ditallowedimethyl ammonium bromide, cetyltrimethyl ammonium hydroxide, and tetradecyltrimethyl-ammonium bromide (TTAB). Nonionic surfactants such as, for example, octylphenol ethylene oxide condensates (e.g., TRITON X-100), and silicone block copolymers (e.g., SILWET) could also be used.

An organic solution containing the desired surfactant is prepared, typically by simply mixing the surfactant with an organic solvent. Illustrative organic solvents include alkanes having at least five carbon atoms such as hexane, isooctane, and octane; aromatic hydrocarbons such as benzene or toluene. The surfactant concentration should be below the critical micellar concentration that would result in a reverse micelle. On the other hand, the surfactant concentration should be sufficient to form the protein-surfactant complex resulting in the solubilization of the protein in the solvent. A particular surfactant concentration range depends on the size of the protein molecule and the hydrophobicity of the surfactant molecule. For example, 1 mM AOT may be used for the solubilization of 1 mg/ml α-chymotrypsin.

The organic surfactant solution then is intimately mixed with the aqueous modified protein solution, typically at room temperature (i.e., about 20-25° C.). The modified protein concentration in the resulting mixture may range, for example, from about 1 μg/ml to about 10 mg/ml. The pH of the resulting mixture may range from about 2 to about 12, depending upon the optimal pH for the bioactivity of the particular protein. The volume ratio of the organic surfactant solution relative to the aqueous modified protein solution can range from about 1:10 to about 10:1. The resulting mixture then is phase-separated by centrifugation or similar techniques. Phase separation can also occur simply by allowing the mixture to rest without performing any additional separation techniques. The modified protein is extracted into the organic phase resulting in the formation of the protein-surfactant complex. The protein-surfactant complex may be isolated by drying or otherwise removing the organic liquid and other components. Additives may be included in the organic/aqueous mixture to provide a higher protein extraction ratio and improved phase separation. For example, inorganic salts such as $CaCl_2$ and KCl may improve phase separation. Hydrophilic small molecules such as 1-propanol and 2-propanol may provide a higher extraction ratio.

With reference back to the general synthesis procedure, the modified polypeptide or protein is contacted with at least one shell-forming compound. A mixture of shell-forming compounds may be simultaneously contacted with the modified polypeptide or protein, or individual shell-forming compounds may be successively or stepwise contacted with the modified polypeptide or protein. As described above, the modified polypeptide or protein may or may not have undergone solubilization treatment prior to contact with the shell-forming compound. The shell-forming compound may be a polymerizable compound that is capable of forming chemical bonds with the modified functional groups on the surface of the polypeptide or protein. The polymerizable compound may be a monomer, an oligomer, a prepolymer, or a polymer that can be further polymerized. A mixture of polymerizable compounds may be used to achieve a variety of properties and characteristics for the polymer shell. The chemical bonding and polymerization with the shell-forming compound can occur in either an organic or aqueous system. For example, if the shell-forming compound is soluble or dispersible in water, then organic solubilization of the modified polypeptide or protein is not necessary, and the polymerization can be performed in an aqueous system. On the other hand, if the shell-forming compound is only soluble or dispersible in an organic solvent, then organic solubilization of the modified polypeptide or protein may be desirable so that polymerization can be performed in an organic system.

According to a representative example, the polymerizable compound includes at least one polymerizable carbon-unsaturated bond and at least one substituted silyl group such as an alkoxysilyl or hydroxysilyl moiety. The polymerizable unsaturated bond may be an α, β-ethylenically unsaturated bond. Examples of such carbon-unsaturated silane compounds (interchangeably referred to herein as "silicate" compounds) may have the representative formula (I):

$$R_a SiX_{(4-a)}$$

wherein each R represents an organic moiety that includes at least one carbon-unsaturated bond and in which a carbon atom is bonded directly to the silicon atom, and; a is an integer from 1 to 3; and each X represents at least one moiety selected from a hydroxyl group, an alkoxy group, a siloxy group, an alkyl group, a carboxyl group, or an amino group; and wherein each R moiety may be the same or different and each X moiety may be the same or different. According to certain examples of the silane compound, at least one of the X moieties is an alkoxy group. Vinyl silanes may be particularly suitable.

More specific examples of silane compounds are (meth)acryloxy-containing organosilanes, more particularly a (meth)acryloxy-containing alkoxysilane having the following representative formula (II):

$$CH_2{=}CH(R^1){-}C(O){-}O{-}(R^2){-}Si(R^3)_a(OR^4)_{3-a}$$

wherein $R^1$ represents hydrogen or a methyl group; $R^2$ represents a divalent hydrocarbon moiety; each $R^3$ represents hydrogen or an alkyl group; each $R^4$ represents an alkyl group; and a is an integer from 0 to 2. $R^2$ may be an alkylene or substituted alkylene group that includes 1 to 10 carbon atoms such as, for example, $-CH_2-$, $-CH_2-CH_2-$, $-CH_2-CH_2-CH_2-$, or $-CH_2-CH(CH_3)-CH_2-$. The alkyl group for $R^3$ or $R^4$ may include 1 to 10 carbon atoms, more particularly 1 to 5 carbon atoms. (Meth)acryloxy-containing organosilanes tend to be more reactive compared to vinyl silanes (e.g., vinyltrimethoxysilane) or allyl silanes (e.g., allyltrimethoxysilane) that do not contain (meth)acryloxy functional groups. Thus, the vinyl group polymerization can be initiated by a relatively reduced amount of initiator, and reach desired completion in a shorter time span.

Illustrative examples of carbon-unsaturated silanes include vinyltrimethoxysilane, vinyltriethoxysilane, vinyltris-(β-methoxyethoxy)silane, γ-methacryloxypropylmethyldimethoxysilane, γ-methacryloxypropyltrimethoxysilane, γ-methacryloxypropylmethyldiethoxysilane, γ-methacryloxypropyltriethoxysilane, γ-acryloxypropyltrimethoxysilane, γ-acryloxypropyltriethoxysilane, vinyltriisopropoxysilane, vinyldimethylmethoxysilane, allyltrimethoxysilane, allyltriethoxysilane, allylaminopropyltrimethoxysilane, allyldimethoxysilane, vinyltributoxysilane, vinyltriisopropoxysilane, vinylmethyldiethoxysilane, and vinylmethyldimethoxysilane.

Acrylic acid and (meth)acrylates are additional examples of polymerizable, shell-forming compounds that could be reacted with a vinyl-functionalized polypeptide or protein molecule in aqueous buffer. Suitable water-soluble acrylates include acrylic acid, methyl acrylate, ethyl acrylate, and butyl acrylate.

In the case of a polyethylene glycol as the protein surface-functionalizing compound, the shell-forming compound may be any compound that can crosslink amino, carboxyl, and/or hydroxyl pendant groups. Such shell-forming compounds include dialdehydes such as glutaraldehyde; isocyanates such as toluene diisocyanate, diphenylmethane diisocyanate; carbodiimides such as 1-ethyl-3-(3-dimethylaminopropyl) carbodiimide hydrochloride (with lysine); polyethyleneimine; glycine; and lysine.

The polymerization of the modified polypeptide or protein with the polymerizable or shell-forming compound may be accomplished by any polymerization mechanism such as, for example, condensation or addition polymerization. In the case of a carbon-unsaturated silane as the shell-forming compound the polymerization occurs in two steps. The first step involves addition polymerization of the α, β-ethylenically unsaturated functional group of the modified polypeptide or protein with the carbon-unsaturated functional group of the carbon-unsaturated silane compound. The second step involves hydrolysis and condensation of the silicon-containing functional groups derived from the carbon-unsaturated silane compound to produce a crosslinked polyorganosiloxane. The final product is a nanoparticle that includes the polyorganosiloxane as a shell covalently bound to the polypeptide or protein molecule.

In an illustrative example, the addition polymerization involves vinyl group polymerization to chain-extend linear polymers on the protein surface. The linear polymers on the protein surface include silyl or substituted silyl pendant groups, particularly alkoxysilyl pendant groups. The addition polymerization typically is free radical-initiated, such as by thermal, photo, or redox free radical initiation. The polymerization may be carried out via bulk, emulsion or solution polymerization, although solution polymerization is the typical media when carbon-unsaturated silane compounds are utilized.

The modified protein may be mixed with the carbon-unsaturated silane compound to form a free radical polymerizable mixture. The free radical polymerizable mixture may include suitable radical initiators such as any thermal, redox or photo initiators. Illustrative initiators include, for example, alkyl peroxides, substituted alkyl peroxides, aryl peroxides, substituted aryl peroxides, acyl peroxides, alkyl hydroperoxides, substituted alkyl hydroperoxides, aryl hydroperoxides, substituted aryl hydroperoxides, heteroalkyl peroxides, substituted heteroalkyl peroxides, heteroalkyl hydroperoxides, substituted heteroalkyl hydroperoxides, heteroaryl peroxides, substituted heteroaryl peroxides, heteroaryl hydroperoxides, substituted heteroaryl hydroperoxides, alkyl peresters, substituted alkyl peresters, aryl peresters, substituted aryl peresters, azo compounds and halide compounds. Specific initiators include cumene hydroperoxide (CHP), t-butyl hydroperoxide (TBHP), t-butyl perbenzoate (TBPB), sodium carbonateperoxide, benzoyl peroxide (BPO), lauroyl peroxide (LPO), methylethylketone peroxide 45%, potassium persulfate, ammonium persulfate, 2,2-azobis(2,4-dimethyl-valeronitrile), 1,1-azobis(cyclo-hexanecarbonitrile), 2,2-azobis (N,N'-dimethyleneisobutyramidine)dihydrochloride, 2,2-azobis(2-amidino-propane)dihydrochloride and 2,2-azobis (2-amido-propane)dihydrochloride. Redox pairs such as persulfate/sulfite and Fe(2+)/peroxide are also useful. The free radical polymerizable mixture may be subjected to suitable free radical initiation conditions such as heat, UV light irradiation, visible light irradiation, electron beam irradiation, plasma, electrolysis and similar free-radical generating schemes. The polymerization conditions (temperature, pH, pressure, etc.) may be readily determined to achieve the desired polymerization.

The molar ratio of the carbon-unsaturated silane compound (e.g., monomer) to the modified polypeptide or protein may be selected to control the desired degree of chain-extension polymerization. More specifically, the ratio of the moles of vinyl functionality in the vinyl silane compound to the moles of vinyl functionality in the modified protein may be controlled. In other words, the proportion of vinyl functional groups that are derivatized with a polymer chain and the length of the polymer chain may be controlled, at least in part, by the silane:protein molar ratio. The molar ratio of the carbon-unsaturated silane compound (e.g., monomer) to the modified polypeptide or protein also may be selected to control the desired degree of crosslinking of the alkoxysilyl functional groups as explained below in more detail. In general, the silane:protein molar ratio may range, for example, from about 20 to about 80,000, more particularly about 200 to about 20,000.

As mentioned above, the shell formation also involves a crosslinking of the silicon-containing functional group in addition to the chain-extension polymerization. The crosslinking may be accomplished, for example, by adding a separate crosslinking agent either during or after the chain extension polymerization (e.g., the vinyl polymerization). However, in certain variants of the processes disclosed herein addition of a separate crosslinking agent is not required in order to achieve the desired limited crosslinking for the individual polymer shells. For example, the addition of a separate crosslinking agent to promote crosslinking of the (meth)acryloxy-containing organosilane compound typically is not necessary. Addition of a separate crosslinking agent also may not be necessary in the case of the silane compounds that do not contain (meth)acryloxy functional groups depending upon the desired degree of crosslinking.

Instead of adding a separate crosslinking agent, the crosslinking can involve hydrolysis and condensation of the silicon-functional group. For example, the alkoxysilyl or hydroxysilyl functional groups can undergo hydrolysis in an aqueous media. Additives such as water-soluble organic solvents and salts may be added to the aqueous media to improve the hydrolysis. In general, the hydrolysis and condensation may be conducted at any temperature provided denaturation of the protein is avoided, but a range of about 4 to about 40° C. may be used as an example. The pH of the hydrolysis aqueous media may be controlled to be acidic, neutral or basic, but a range of about 2 to about 11 may be used as an example. Typically, the pH of the hydrolysis/condensation is at or relatively near the optimal pH of the protein for bioactivity. Buffer salts, acids, and/or bases may be used to control the pH. Examples of acids that may be added include organic acids such as acetic acid and the like, and an inorganic acid such as hydrochloric acid, sulfuric acid, phosphoric acid and the like. Examples of an alkali that may be added include sodium hydroxide, potassium hydroxide and the like. A catalyst or an additional silicon-containing compound (e.g., tetraethyl orthosilicate) may be added to enhance the hydrolysis/condensation of the intermediate product.

The intermediate polymerization product that includes the alkoxysilane or hydroxysilane functional groups may only be soluble in an organic solvent. Thus, addition of an aqueous buffer solution to the organic phase-intermediate polymerization product results in a two-phase system. The modified protein particles undergo hydrolysis and condensation, causing movement of the hydrolyzed and condensed product from the organic phase and into the aqueous phase. In other words, the hydrolyzed and condensed product is, in effect, extracted from the organic phase into the aqueous phase. The aqueous phase and the organic phase are separated via any appropriate separation technique. The aqueous phase then is filtered as described below in more detail to separate agglomerations and other particles larger than nanoparticle size, resulting in a filtrate that includes substantially only particles of nanoparticle size. This extraction and filtration process may be repeated until no significant amount of protein activity is observed in an extraction filtrate. At this point, no additional extractions are performed. Each one of the previously obtained extraction filtrates are then mixed together to produce a final product. The final product containing the nanoparticles may be aged by placing the final product in an ambient temperature of about 4 to about 30° C. for an extended period of time such as, for example, at least about 24 hours.

As mentioned above, acrylic acid or a (meth)acrylate is another monomer that can be reacted with a vinyl-functionalized polypeptide or protein molecule. This addition polymerization could be performed in an aqueous buffer. The vinyl-functionalized polypeptide or protein can be mixed with water-soluble acrylic acid or (meth)acrylate in an aqueous buffer, and the vinyl polymerization can be initiated by UV radiation in the presence of an initiator such as azobisisobutryonitrile. The polymerization product is a heterogeneous population that includes large polymers or agglomerations as well as nanoparticles having an acrylic polymer shell covalently bound to the polypeptide or protein molecule. The nanoparticles can be isolated via filtration from the heterogeneous population of polymeric products.

Polyethylene is another modifier compound described above. In this case, the dialdehyde, isocyanate, or carbodiimide shell-forming compound causes crosslinking of the grafted polyethylene glycol-containing amino groups. Polyethylene glycol (PEG) grafted with epoxy groups or maleic anhydride groups can be further crosslinked in the presence of L-glycine. Another path is to employ a block copolymer of PEG-alkoxysilane. The PEG domain of the block copolymer can be attached to the protein molecule via a grafted epoxy or maleic anhydride group, and the alkoxysilane will be hydrolyzed and condensed to form a shell around the protein molecule. The final product is a nanoparticle that includes the crosslinked polyethylene structure as a shell covalently bound to the polypeptide or protein molecule.

As mentioned previously, there is another synthetic approach that was referred to as option (b) above. In this approach, the polypeptide or protein modifier compound is itself a silane compound. A modifier compound that includes an α, β-ethylenically unsaturated functional group is not required. Instead, a functional group of the silane compound is directly covalently bonded to the free amino, carboxyl, and/or sulfide groups at the surface of the polypeptide or protein molecule. Illustrative silane compounds that can serve as modifier compounds are those that also include a group that is reactive with free amino, carboxyl, and/or sulfide groups of the protein molecule. Such amino and carboxyl-reactive groups are described above in connection with the modifier compound used in the option (a) synthesis approach. Specific examples in the case of silane compounds include succinyl groups (e.g., succinic anhydride-bearing silanes), an amino group, an epoxy group, or an isocyanato group. Bonding of the succinic anhydride group to the amino group of the polypeptide or protein molecule can occur by contacting the succinic anhydride-bearing silane with the polypeptide or protein molecule in an aqueous buffer solution. Bonding of the amino group of the silane compound with the amino group of the polypeptide or protein molecule can occur via reaction of the polypeptide or protein with the amino silane compound in the presence of glutaraldehyde, toluene diisocyanate, or diphenylmethane diisocyanate in slightly basic aqueous conditions. The result is the formation of a glutaraldehyde or isocyanate linkage, respectively, between the amino groups.

Polyethylene glycol compounds that have been modified to include at least one silyl or substituted silyl group are additional examples of silane compounds that can be used in the option (b) synthesis procedure. As described above, polyethylene glycol compounds can be covalently grafted onto polypeptide or protein molecules.

The resulting bonded silane compound provides silyl or substituted silyl functional groups on the surface of the polypeptide or protein molecule. The silyl or substituted silyl functional groups can then be crosslinked via hydrolysis and condensation as described above to form the polysiloxane shell. One feature of the option (b) approach is that water-soluble silane compounds can be used. Illustrative water-soluble silane compounds include 3-(triethoxysilyl)propyl-succinic anhydride, aminopropyltriethoxysilane, aminopropyltrimethoxysilane, aminopropoysilanetriol, 3-aminopropyltris(methoxyethoxyethoxy)silane, N-(triethoxysilylpropyl)-O-polyethylene oxide urethane, N-(3-triethoxysilylpropyl)gluconamide, methacryloxypropyltris (methoxyethoxy)silane, isocyanatopropyltriethoxysilane, epoxypropoxytriethoxysilane, epoxyhexyltriethoxysilane, γ-glycidoxypropyltriethoxysilane, and γ-glycidoxypropylmethyldiethoxysilane.

The resulting final synthesized product may be considered to be a protein/polymer biocomposite. The desired nanoparticle-sized biocomposites may be isolated from the final synthesis product mixture or solution, for example, via centrifuging, filtration, adsorption, absorption and similar separation or purification techniques. According to certain examples, the final synthesis product includes solid protein/polymer biocomposites dissolved, suspended or dispersed in a liquid media. The biocomposite-containing liquid is passed through at least one filter having a maximum pore size of 1 µM, more particularly a maximum pore size of 0.2 µm, and more particularly a maximum pore size of 0.1 µm. Examples of such filters include membrane filters such as syringe filter units. Any membrane filters that can separate proteins based on their molecular weight can also be used, such as filters having a respective molecular weight cut off ("MWCO") of 3 kilodaltons, 10 kilodaltons, 30 kilodaltons, 50 kilodaltons, and 100 kilodaltons. Any protein/polymer agglomerates and impurities having a dimension greater than the respective maximum pore size (e.g., greater than 1 μm), of course, will be retained on the filter. Thus, only nanoparticle-sized biocomposites will be present in the filtrate. According to one particular example, the resulting filtrate can be washed on a filter having a desired MWCO in order to separate material that is too small to be a protein nanocomposite. The concentration of biocomposite nanoparticles may be adjusted, for example, by increasing or decreasing the polypeptide or protein concentration during the initial synthesis steps or during the washing of the final synthesis product on a filter membrane. It should be understood that filtration is not the only technique available for isolating the biocomposite nanoparticles, and that other separation techniques such as those mentioned above could be used.

It also should be recognized that any of the intermediate products generated during any of the syntheses disclosed herein also may be subjected to separation techniques for isolating nanoparticle-sized intermediate products. Such nanoparticle-sized intermediate products then can be employed for the subsequent synthesis steps. For example, mixing an aqueous glutaraldehyde solution with a protein molecule solution in an aqueous buffer (pH about 7-10, temperature of about 4° C. to room temperature) may generate a wide range of crosslinked protein particles. The nanoparticle-sized particles may be separated with a membrane filter as described above. The generation of such nanoparticles via glutaraldehyde may be especially applicable for producing shell nanoparticles having containing than one protein molecule in the core construct as described above. The glutaraldehyde-treated nanoparticles may then be subjected to further synthesis for forming the shell around the nanoparticles.

The biocomposite nanoparticles can be provided in powder form, for example, by introducing a large quantity of salts (e.g., KCl, NaCl, sodium phosphate, potassium phosphate, etc.) into the above-described, final nanoparticle-containing solution. The amount of added salt may vary widely, but could range from about 40 to about 99 weight %. The resulting mixture then can be subjected to lyophilization techniques to produce the powder.

According to one variant on the use of the nanoparticles, the isolated biocomposite nanoparticles may be subjected to further crosslinking to form a matrix of crosslinked nanoparticles, wherein each of nanoparticles retains its individual covalently-bound shell. For example, if the shell is a polyorganosiloxane, a mixture of the nanoparticles may be subjected to further silanol condensation or an additional silane compound may be reacted with the nanoparticles to effect crosslinking between the polymer shells of the nanoparticles.

Figure 1:
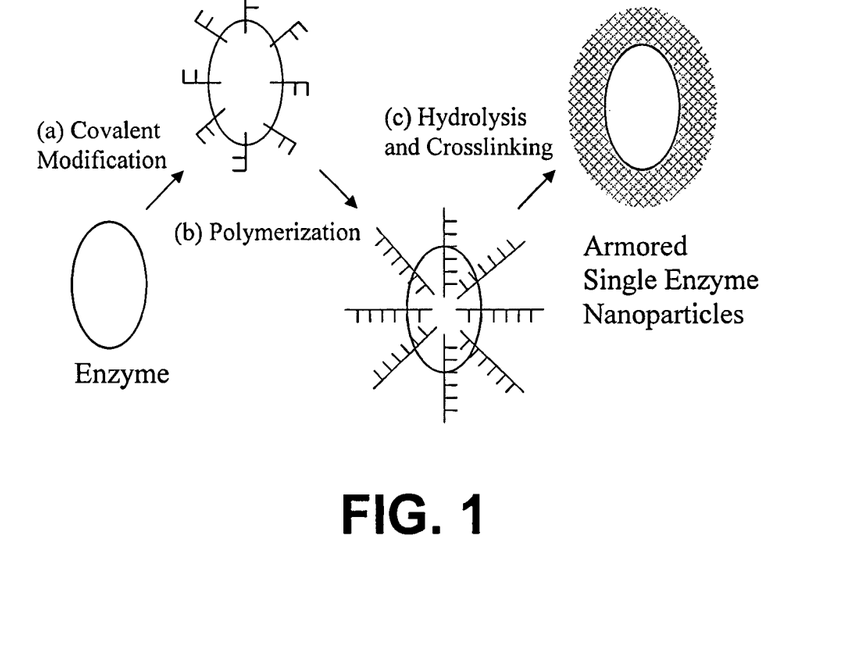
FIG. 1 is a schematic diagram of one example of synthesizing biocomposite nanoparticles.
Figure 2:
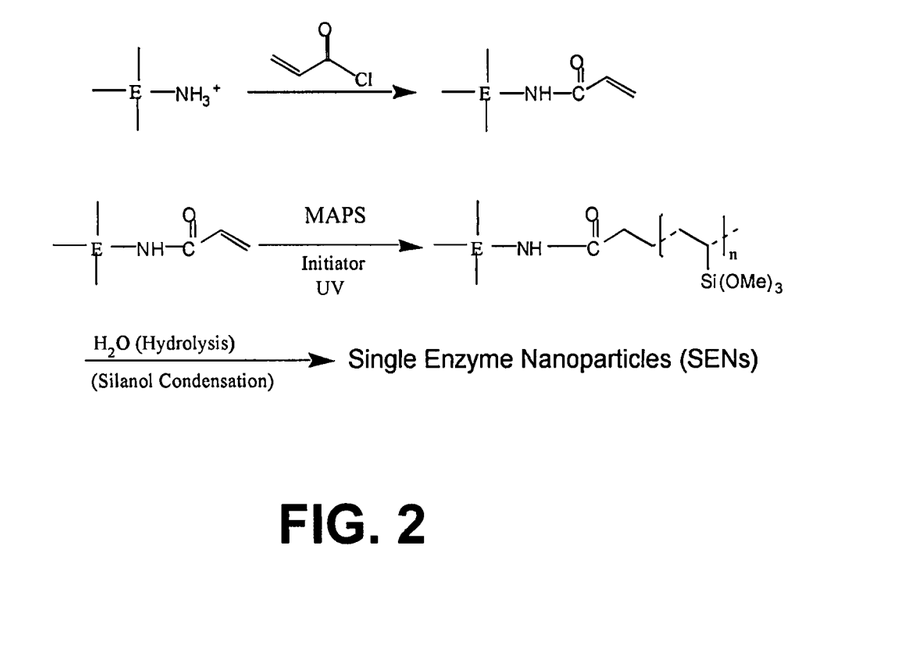
FIG. 2 shows the chemical synthesis of one example of biocomposite nanoparticles.

An exemplification of the above-described synthesis is depicted schematically in FIG. 1 and chemically in FIG. 2. Vinyl modification is introduced onto the surface of an enzyme molecule (designated "E" in FIG. 2) via reaction of acryloyl chloride with the free amino groups of the enzyme molecule. The vinyl-modified enzyme molecule is reacted with a silane monomer, methacryloxypropyltrimethoxysilane ("MAPS"). The resulting intermediate product is an enzyme molecule that has been derivatized to include polymer chains at the sites of the modified free amino groups. The number n of repeating monomer units in the polymer chain may range, for example, from about 3 to about 100, more particularly from about 5 to about 20. The polymer chain in the intermediate product includes pendant trimethoxysilyl groups. These trimethoxysilyl groups then undergo hydrolysis and condensation to generate a single enzyme nanoparticle ("SEN").

A feature of certain examples of the above-described syntheses is that the yield of biocomposite nanoparticles may range from about 35% to about 95%, more particularly from about 50% to about 80%, based on the bioactivity of the protein in the biocomposite nanoparticle divided by the initial bioactivity of the free or native protein prior to synthesis of the biocomposite nanoparticle. There are various options for increasing the yield. For instance, in the variation that involves free radical polymerization, the concentration of free radical initiator may be reduced to increase the yield of nanoparticles. As an illustrative example, the free radical initiator concentration may range from about 0.1 to about 10 weight %, based on the total amount of modified protein and carbon-unsaturated silane compound. The amount of time in which the shell-forming polymerization is permitted to occur also can affect the yield. In general, the yield will increase with shorter reaction times for the shell-forming polymerization. A further factor increasing the yield is the iterative extraction performed during the hydrolysis and condensation of the silyl or substituted silyl functional groups.

Figure 6:
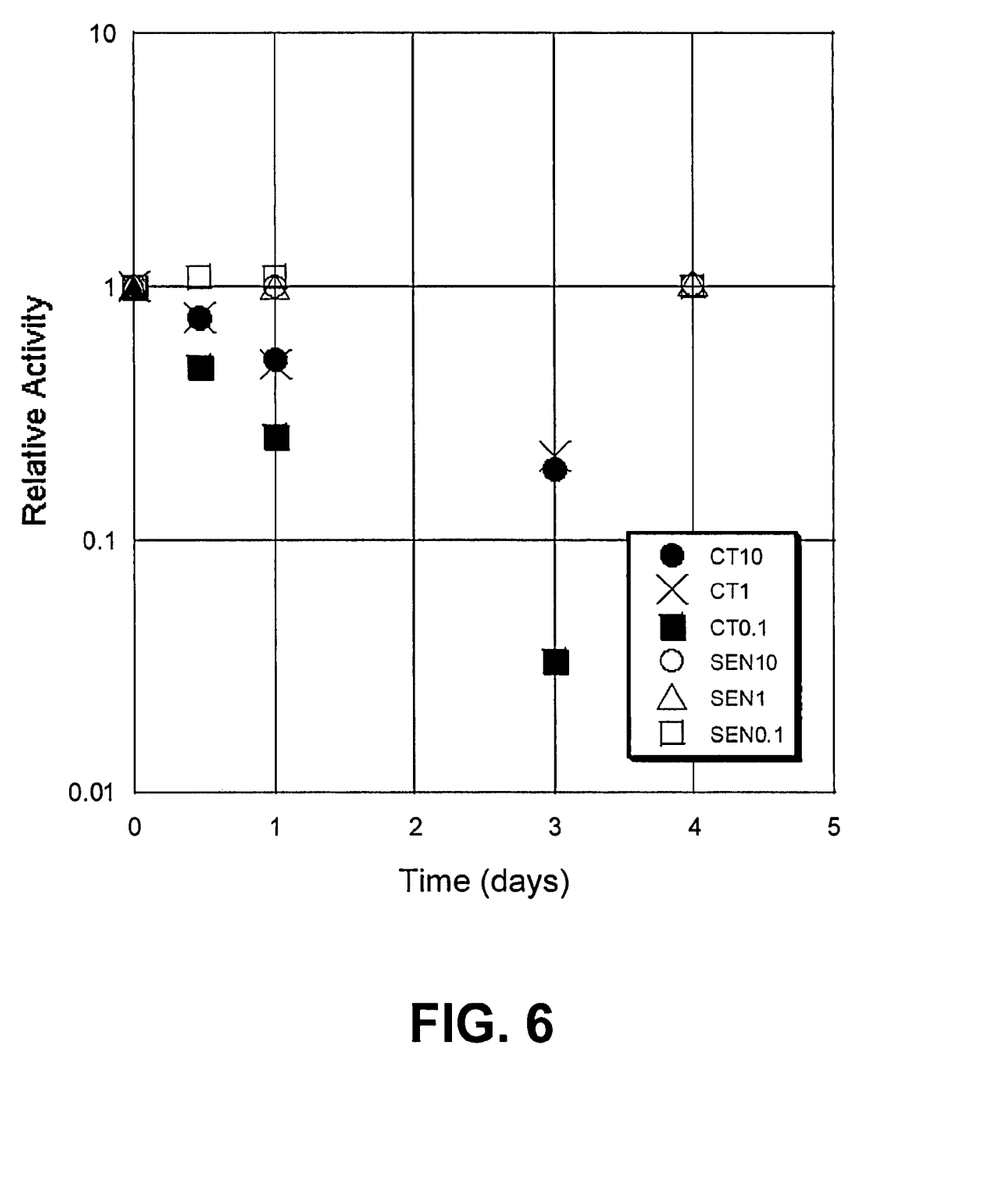
FIG. 6 is a graph depicting the stability of α-chymotrypsin biocomposite nanoparticles (○, 10 μg/ml; Δ, 1 μg/ml; ⌀, 0.1 μg/ml) and free CT (●, 10 μg/ml; x, 1 μg/ml; ■, 0.1 μg/ml). Residual activity was determined by the hydrolysis of TP in aqueous buffer (10 mM sodium phosphate, pH 7.8) after incubation at 30° C. All the incubation was done in plastic tubes since the α-chymotrypsin biocomposite nanoparticles covalently bound to the inner surface of glass vials.

The activity and stability of the polypeptide or proteins in the biocomposite nanoparticles may be readily determined, for example, by various enzymatic reactions with various substrates. In the example of $\alpha$-chymotrypsin, the proteolytic activity may be measured, for example, by a hydrolysis assay of N-succinyl-Ala-Ala-Pro-Phe p-nitroanilide ("TP"). Examples of biocomposite nanoparticles having a protease molecule core as disclosed herein may have a relative bioactivity stability of at least about 0.9 for at least about ten days, more particularly a relative bioactivity stability of at least about 1.0 for at least about four days. The relative bioactivity is measured as the ratio of residual activity to initial activity (see FIG. 6 explained in more detail below). The stability of the disclosed biocomposite nanoparticles can extend the lifetime of enzymes in various applications such as biosensors, bioremediation, detergents, enzymatic synthesis in the pharmaceutical and food industries, and bio-hydrogen production from renewable bio-products.

The unique composition and structure of the nanoparticles described herein can serve as the building blocks for further structures and materials. Reactions with the surface of the nanoparticles, either as synthesized or after further covalent modifications, can bond the nanoparticles to other molecules, macromolecules, particles, or materials. The biocomposite nanoparticles may be bonded to other biocomposite nanoparticles. The biocomposite nanoparticles may be bonded to nanoparticles of other materials such as metals, magnetic materials, metal oxides and plastics. The biocomposite nanoparticles may be bonded to micron-size particles of other materials such as metals, magnetic materials, metal oxides, and plastics. The biocomposite nanoparticles may be bonded to other nanostructures such as nanotubes. The biocomposite nanoparticles may be bonded to macromolecules such as DNA, RNA, proteins, polysaccharides, or synthetic polymers. The combination of biofunctional nanoparticles, such as single enzyme nanoparticles, to other structures and materials provides a means to create multifunctional assemblies.

For example, a feature of a polyorganosiloxane shell is that it can be readily modified to include other classes of chemical functionalities. The modification may be accomplished, for example, by using a vinyl silane monomer that also includes the desired additional functionality. The modifying vinyl silane monomer may be added during the vinyl polymerization or it may be added during the hydrolysis and condensation of the silicon-containing functional groups.

One desirable chemical functionality that can modify the shell is a group that can impart solubility in a selected solvent. The solvent may be a hydrophobic solvent or a hydrophilic solvent. A solubilized nanoparticle can offer the advantage of increased interaction between the protein molecule in the core and a reaction media. As a further illustration, the shell could be modified to enhance its ability for attaching to surfaces, macromolecules, or biological substrates. For example, amino groups could be grafted onto the nanoparticle shell. The amino-grafted nanoparticles then can be covalently bonded to amino-grafted deoxyribonucleic acid (DNA) via linkers such as glutaraldehyde. According to an additional variant, the shell of a first nanoparticle and the shell of a second nanoparticle each could be modified so that they can be covalently bonded with each other resulting in multifunctional nanoparticle assemblies. Following another approach, a mixture of different enzyme nanoparticles could be prepared and then consolidated such as, for example, by precipitation, by evaporating the solvent, or by adding crosslinking agents to connect one nanoparticle with another. Consequently, the multiple differing enzymes would be in very close proximity to each other, with their separation being defined by the thickness of two of the individual nanoparticle shells. Such close proximity will enhance the sequential conversion of a molecule by the different enzymes compared to enzymes scattered in dilute liquids or mixtures of larger than nanoscale particles.

The thin and porous structure of the "armored" polymer shell allows for aqueous solubility of the biocomposite nanoparticles. This water-soluble feature can be used for homogeneously immobilizing biocomposite nanoparticles on substrate surfaces, particularly nanostructured matrices such as nanoporous silica, carbon nanotubes, and conductive polymers. The immobilization of the biocomposite nanoparticles will be extremely useful in various applications such as biosensing and bioconversion, since enzymes can be stabilized and the nanostructured matrices will provide a large surface area for the attachment of the biocomposite nanoparticles. The immobilized biocomposite nanoparticles make it easy to purify the products after each bioconversion, and can be easily recovered for the next-step bioconversion.

One specific example of a use for the enzyme nanoparticles involves bioconversion of various substrates via enzymatic catalysis. Desirable applications include degradation of toxic substances for bioremediation, and synthesis of various chemicals such as drug intermediates and peptides. Conversion of the substrate to product may be controlled by techniques such as those described in U.S. Pat. No. 5,719,039, which also describes various substrates suitable for enzymatic catalysis in assorted organic solvents.

Further specific uses of the enzyme nanoparticles include hydrolysis and/or transesterification of drug intermediates; enzymatic detergents; conversion of glucose to fructose (e.g., utilizing glucose isomerase); bioremediation employing laccase, tyrosinase, peroxidase, organophosphorous hydrolase, or dehalogenase for the decontamination of organic contaminants such as phenols, pesticides, and halogenated compounds; biosensing using glucose oxidase, peroxidase, tyrosinasse, or organophosphorous hydrolase; and hydrogen production using glucose dehydrogenase and hydrogenase.

An additional application involves the use of trypsin nanoparticles for trypsin digestion in proteomic analysis. In the proteomic analysis of proteins in a sample, trypsin is employed for digesting proteins into peptides. The trypsin digestion takes a long time (usually an overnight incubation), and is difficult to automate due to the poor stability of trypsin. The improved trypsin stability provided by the nanoparticle construct disclosed herein may prolong the lifetime of the trypsin, and thus reduce the incubation time.

Immobilization of the biocomposite nanoparticles on substrate surfaces also offers a number of opportunities. For example, the polyorganosiloxane shells may be readily adhered to silicate surfaces (e.g., glass, silicon wafer, and quartz) due to the presence of silyl groups in the polyorganosiloxane shells. In this case, the biocomposite nanoparticles may be provided in a suitable carrier media such as an aqueous solution, and then the aqueous solution can be applied to the substrate surface. Drying of the aqueous solution will produce biocomposite nanoparticles immobilized on the substrate surface. Protein chips often are constructed from silicate materials, and thus the biocomposite nanoparticles could be adhered to the surface of a protein chip. Adherence to other types of surfaces can be accomplished by grafting desired functional groups into the silicon-containing polymer shell molecular structure during the shell polymerization and formation. For example, the surface of the polymer shell could be functionalized with amino groups by including aminopropyltrimethoxysilane during the hydrolysis/condensation of the silyl or substituted silyl groups.

EXAMPLES

Example 1

Synthesis of Single Enzyme Nanoparticles that Contain α-Chymotrypsin ("SEN-CT")

Modification and Solubilization of CT.

The modification and solubilization of CT were performed by adding 10 mg CT to 5 ml of phosphate buffer (0.2 M sodium phosphate, pH 8.0). The enzyme solution was cooled to 0° C., and 4 μl of acryloyl chloride was gradually added to the solution over 10 minutes in a stirring condition. The acryloylated CT was recovered by gel filtration chromatography (Sephadex G-25 gel, 100-300 μm).

Ten milliliters of an aqueous enzyme solution (containing 1 mg/ml acryloylated CT, 1% (v/v) isopropanol, and 2 mM $CaCl_2$ dissolved in 10 mM Bis-Tris buffer, pH 7.8) was contacted with an equal volume of hexane containing 2 mM AOT surfactant. The resulting two-phase mixture was stirred vigorously at 22° C. for 5 minutes, and centrifuged at 7000 G for 10 minutes. Upon separation of the hexane phase from the aqueous solution, the enzyme-surfactant complex was dried by evaporating hexane with nitrogen-bubbling or under vacuum, and then reconstituted back into hexane when used for the further synthesis of SEN-CT. The concentration of CT in the hexane phase was determined by UV absorption at 280 nm.

Two-Step Polymerization.

MAPS (297 μl) was added to 3 mg solubilized and acryloylated CT in 1.5 ml hexane. Vinyl group polymerization between MAPS and acryloylated CT was initiated by UV light (365 nm) in the presence of the free radical initiator 2,2'-Azobis-(2,4-dimethylvaleronitrile) (0.8 mg/ml). Polymerization was performed under UV illumination in a black box at room temperature overnight, and some population of resulting polymers precipitated out in the form of a white powder.

Subsequent hydrolysis and condensation of the trimethoxysilyl groups was accomplished by adding an equal volume of phosphate aqueous buffer (200 mM phosphate buffer, pH 8.0) to the hexane phase of the vinyl group polymerization that contains the intermediate polymeric products. The resulting two-phase system was vortexed and shaken at 22° C. and 300 rpm for 5 minutes. The aqueous buffer phase was removed from the two-phase system by a syringe. The aqueous buffer phase was filtered by a syringe filter unit (with maximum pore size 0.1 μm), and produced a filtrate consisting of a transparent solution that turned into a turbid solution within 10-30 minutes. This extraction process was iterated (typically by about four to five times) until no significant amount of CT activity was observed in the aqueous extraction filtrate in the latest iteration. At this point, no more extractions were performed. The individual extraction filtrates that were obtained in each iteration were then mixed together to produce a final extracted aqueous buffer solution. The extracted aqueous buffer solution contained the majority of the active CT (at least about 85%), and was aged in the refrigerator at least for a day. The aged and turbid solution was filtered again by the syringe filter unit (with maximum pore size 0.1 μm), and further washed excessively by buffer (10 mM phosphate buffer, pH 7.8) on a membrane filter (MWCO 10K: molecular weight cut-off 10,000). This washing process should remove the autolytic products of CT and un-reacted agents such as MAPS and initiators. The final clear solution (having a fairly homogeneous population of SEN-CT) contains most of the initial active CT, and was stored in a refrigerator (4° C.). The yield of active CT in the form of SENs was 38-73% (calculated based on the total final activity of SEN-CT/the total initial activity of native CT before synthesis=0.38−0.73)

Example 2

TEM Imaging of the Biocomposite Nanoparticles

Figure 3:
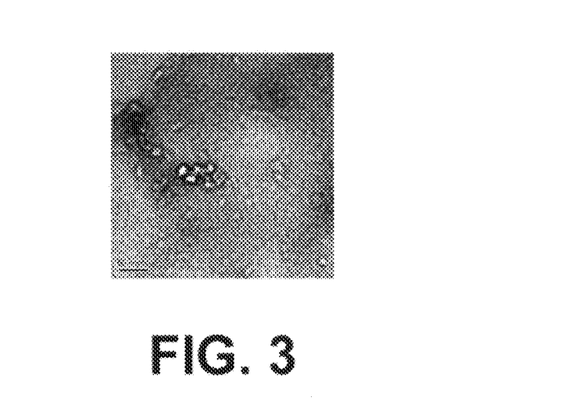
FIGS. 3, 4 and 5 are transmission electron microscopy ("TEM") images of examples of biocomposite nanoparticles. The scale bars in the bottom left corners of the images represent 50 nm (FIG. 3) and 100 nm (FIGS. 4 and 5), respectively.
Figure 4:
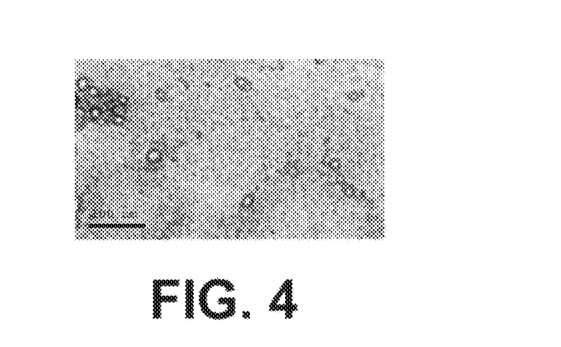
Figure 5:
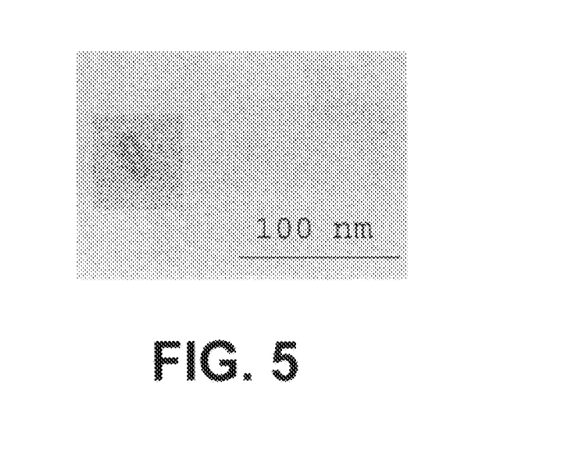

Transmission electron microscopy ("TEM") images of the biocomposite nanoparticles containing α-chymotrypsin ("CT") synthesized as described above are shown in FIGS. 3, 4 and 5. The seemingly hollow center of the nanoparticle matches the size and shape of the CT, and results from the transmittance of the electron beam through the protein structure. The dark image surrounding the CT core is the polymer "armored" shell, and the presence of silicon was confirmed by energy dispersive x-ray analysis in the TEM instrument. It is apparent from the images of FIGS. 3, 4 and 5 that the nanoparticles do not have a dimension greater than about 30-40 nm, and in some cases, 10-20 nm. FIG. 5 is of interest since it shows two protein molecules in the core of the nanoparticle.

The TEM images were obtained by further washing the final samples of the SEN-CT with distilled water on a membrane filter (MWCO 10K). The washed samples were observed under a JEOL 2010 high-resolution analytical electron microscope (JEOL USA Inc., Peabody, Mass.). Various concentrations of SEN-CT were tested to obtain the images of the biocomposite nanoparticles, which show the discrete nanoparticles, but also contain a large number of nanoparticles. In other words, a rigorous optimization of SEN-CT concentration was performed to prevent two extremes: excessively high concentration resulting in the images of a black layer having a lot of hollow spots; and insufficiently low concentration to capture a large number of SEN particles in an image. The presence of silicon in the armored shell of SEN-CT, which represents the success of the SEN synthesis, was confirmed by the energy dispersive X-ray analysis in the TEM instrument.

Example 3

Activity and Stability of the Biocomposite Nanoparticles

The CT activity was determined by the hydrolysis of N-succinyl-Ala-Ala-Pro-Phe p-nitroanilide ("TP") (1.6-160 μM) in an aqueous buffer (10 mM phosphate, pH 7.8) at room temperature (22° C.). The absorbance increase at 410 nm was monitored using a spectrophotometer (Model Cary 5G UV-Vis-NIR spectrophotometer from Varian Inc., Palo Alto, Calif.), and converted to the initial hydrolytic rate at each substrate concentration. Kinetic constants ($k_{cat}$, $K_m$, and $k_{cat}/K_m$) were obtained by using software (Enzyme Kinetics Pro from ChemSW, Farifield, Calif.) that performs nonlinear regression based on the least square method.

The active site concentration of both free CT and SEN-CT was determined by the MUTMAC assay. In a typical procedure, 100 μl of free CT or SEN-CT solution in various concentrations (10-1000 μg/ml) was mixed with 2 ml of 25 μg/ml MUTMAC solution (0.1 M sodium phosphate, pH 7.8). The fluorescence emission at 450 nm (excitation at 360 nm) was measured using a PTI fluorescence system (Lawrenceville, N.J.) after the emission intensity reached the plateau. A solution of 4-methylumbelliferone was used as the standard. BCA assay (Pierce, Rockford, Ill.) was used to determine the protein content in the CT sample. Tests with the out-of-bottle CT powder showed that 52.4 weight % was active by the active site titration. On the other hand, SEN-CT resulted in 41.2 weight % active CT, and it suggests that 11.2 weight % of the initial active CT was damaged during the SEN synthesis.

To assess the CT stability, residual activity was determined (in the same way as mentioned earlier for the enzyme activity measurements) after incubation in aqueous buffer (10 mM phosphate, pH 7.8) at 30° C. for the pre-determined time intervals. In brief, a measured amount of CT sample was added to aqueous buffer in a centrifuge tube, and placed in a temperature-controlled incubator. After a pre-determined incubation time, the tube was removed from the incubator and cooled to the room temperature. 10 μl of TP solution (10 mg/ml in DMF) was added directly to the diluted aqueous enzyme solution in a cuvette, and the reaction rates were measured. For all tests, free CT was used directly from the bottle, and SEN-CT was used from the stock solution in aqueous buffer (10 mM phosphate, pH 7.8).

The stability of the CT biocomposite nanoparticle surprisingly did not show any decrease in CT activity after four-day incubation in a buffer solution at 30° C., while free CT was inactivated very rapidly by an order of magnitude (see FIG. 6). The CT biocomposite nanoparticle started to show about a 5-10% decrease of CT activity after ten-day incubation. The inactivation of free CT was dependent upon the initial CT concentration, and showed a pseudo-first-order inactivation kinetic. Although not bound by any theory, it is believed that the stabilization of the nanoparticle approach may be achieved via the prevention of enzyme molecules from being denatured since the activity of SEN-CT is comparable to free CT in both the hydrolysis of TP and the proteolysis of various proteins (described in more detail below). The crosslinked and armored polymer shell plays a key role in this protection of enzyme molecules.

The storage stability of the CT biocomposite nanoparticles was also impressive in a buffer solution. After a three-month storage of the SEN-CT in the buffer solution (10 mM phosphate buffer, pH 7.8) at 4° C., 82% of the SEN-CT activity remained in solution, and 18% of the CT activity disappeared. However, it was noted that a transparent layer of SEN-CT was built up on the inner surface of the vials. A potentially significant portion of the absent 18% CT activity in the solution should have been transported to the SEN-CT layer, which showed at least an appreciable amount of stable CT activity.

As described above, the activity of SEN-CT and free CT was measured by the hydrolysis of N-Succinyl-Ala-Ala-Pro-Phe p-nitroanilide (TP) in a buffer solution (10 mM phosphate buffer, pH 7.8). The kinetic constants ($k_{cat}$, $K_m$, and $k_{cat}/K_m$) were obtained via nonlinear regression based on the least square method (Table 1). The catalytic efficiency ($k_{cat}/K_m$) of CT in the form of SENs was decreased by about half, and it was due to reduced $k_{cat}$. However, the binding constant ($K_m$) of SEN-CT was almost the same as that of free CT (i.e., the OEF was 0.97). This suggests that the armored polymer shell did not cause any significant mass-transfer limitation for the substrate (TP).

TABLE 1

Kinetic constants of Free CT and SEN-CT in aqueous buffer.[a]

| Sample | $k_{cat}$ (s$^{-1}$)[b] | $K_m$ (µM) | $k_{cat}/K_m$ (×10$^5$ M$^{-1}$s$^{-1}$)[b] |
|---|---|---|---|
| Free CT | 29.9 ± 0.7 | 38.9 ± 2.7 | 7.70 ± 0.06 |
| SEN-CT | 13.8 ± 0.6 | 40.2 ± 4.6 | 3.44 ± 0.04 |
| SEN-CT/Free CT | 0.46 | 1.03 | 0.45 |

[a] The CT activity was determined by the hydrolysis of TP (1.6-160 µM) in an aqueous buffer (10 mM phosphate, pH 7.8) at room temperature (22° C.). The absorbance increase at 410 nm was monitored using a spectrophotometer, and converted to the initial hydrolytic rate at each substrate concentration. Kinetic constants ($k_{cat}$, $K_m$, and $k_{cat}/K_m$) were obtained by using software (Enzyme Kinetics Pro) that performs nonlinear regression based on the least square method.
[b] The active site concentration was determined by the MUTMAC assay. In a typical procedure, 100 µl of free CT or SEN-CT solution in various concentrations (10-1000 µg/ml) was mixed with 2 ml of 25 µg/ml MUTMAC solution (0.1M sodium phosphate, pH 7.5). The fluorescence emission at 450 nm (excitation at 360 nm) was measured after the emission intensity reached the plateau. A solution of 4-methylumbelliferone was used as the standard.

Example 4

Effective Porosity of Biocomposite Nanoparticles

The effective porosity of the CT biocomposite nanoparticles was investigated by the proteolytic activity of CT against various proteins (insulin, apomyoglobin, aldolase, and albumin). The proteolytic activity was measured by the OPA assay, in which OPA reacts with primary amines, formed by the proteolytic cleavage of peptide bonds, and fluoresces ($\lambda_{ex}$=347 nm; $\lambda_{em}$=445 nm). In brief, 100 µl of 1 mg/ml target protein was mixed with 10 µl of 0.1 mg/ml free CT or 0.2 mg/ml SEN-CT [to maintain the similar proteolytic activity] in aqueous buffer (10 mM phosphate buffer, pH 7.8), and incubated at 40° C. After a pre-determined incubation time, the aliquot (10 µl) from each sample was diluted (1/100) in 1 ml borate buffer (200 mM sodium borate buffer, pH 9.5), and the proteolysis was stopped by adding 100 µl of PMSF solution (2 mg/ml in isopropanol). 0.75 ml of diluted sample was mixed with 1.5 ml OPA reagent solution (Sigma P0532, complete reagent containing both OPA and 2-mercaptoethanol). The fluorescence emission at 445 nm (excitation at 347 nm) was measured after the OPA reaction was allowed to proceed at room temperature (22° C.) for 2 minutes. The initial rate of proteolysis (Em445/h) was obtained from the increase of fluorescence emission within 1-3 hours, and converted to the initial rate of amino-group formation (µM/h) based on the result of OPA assay with L-tyrosine standard.

To assess the effective porosity of SEN-CT, we incubated various proteins together with SEN-CT. Since CT is a protease, the proteolytic products can be detected when the substrate proteins can pass through the armored polymer shell of SEN-CT. All substrate proteins were carefully selected, and are of the highest purity (standard proteins for the purpose of calibrating and testing mass spectrometers). No impurities should be in the substrate proteins since the proteolysis of impurities can mask off the proteolysis of target proteins. The detection of proteolytic products was performed by the OPA (orthophthaldialdehyde) method, measuring the amount of amino groups, which are formed by the proteolytic activity of CT. The increase of emission at 445 nm (excitation at 347 nm) was measured time-dependently, and converted to the initial rate of amino-group formation. The initial rates are compared to those with free CT (see Table 2). There was no critical difference between free CT and SEN-CT in their proteolytic activity against various proteins even though there are some variations. This suggests that the effective porosity of SEN-CT is large enough for SEN-CT to be active against large protein such as bovine serum albumin (molecular weight 66 kilodaltons).

TABLE 2

Proteolysis of various proteins by free CT and SEN-CT.[a]

| Protein | Source | MW | µM[b] | Initial Rate with Free CT (µM/h) | Initial Rate with SEN-CT (µM/h) |
|---|---|---|---|---|---|
| Insulin | Bovine | 5734.51 | 159 | 31 | 20 |
| Apomyoglobin | Equine | 16952.27 | 54 | 4 | 13 |
| Aldolase | Rabbit Muscle | 39212.28 | 23 | 30 | 19 |
| Albumin | Bovine Serum | 66430.09 | 14 | 43 | 49 |

[a] The proteolysis was measured by the OPA assay. Each substrate protein (100 µl of 1 mg/ml) was mixed with 10 µl of 0.1 mg/ml free CT or 0.2 mg/ml SEN-CT to maintain the similar initial activity, and incubated at 40° C. After a pre-determined incubation time, the aliquot (10 µl) from each sample was diluted into 1 ml borate buffer (200 mM sodium borate buffer, pH 9.5), and the proteolysis was stopped by adding 100 µl of PMSF solution (2 mg/ml in isopropanol). The portion of diluted sample (0.75 ml) was mixed with 1.5 ml OPA reagent solution, and the fluorescence emission at 445 nm (excitation at 347 nm) was measured after the OPA reaction for 2 minutes. The initial rates of proteolysis were calculated from the time-dependent emission increase, based on the OPA assay with the L-tyrosine standard.
[b] Initial concentration of each substrate protein [0.91 mg/ml] in the incubation solution with CT.

Example 5

Polyethylene Glycol (PEG)/Protein Nanoparticles

Epoxy functional groups can be grafted onto PEG (non-functionalized, $MW_n$ ca 200-10,000) via reaction with epichlorohydrin in an aqueous buffer (pH of about 2-12) or an organic solvent such as methanol. The resulting epoxy-PEG can be contacted with protein molecules in an aqueous buffer (pH of about 7-10). The amino groups on the surface of the protein molecules will react with the epoxy group of the epoxy-PEG, and form protein-linear PEG composites. The protein-linear PEG composites in the aqueous buffer may subsequently be excessively washed on a first membrane filter having a maximum pore size of 0.1 µm and then on a second filter having a lower MWCO of 10K. The filtered product then can be mixed with a polyethyleneimine (PEI) solution in buffer (pH about 2-12), and shaken at about 50 to about 250 rpm for a time period ranging from about 10 minutes to about 2 hours until the PEI can be entangled with the PEG structure around the protein molecules. After excessive mixing, glutaraldehyde treatment (1-5% glutaraldehyde for about 10 minutes or 2 hours) may be performed to crosslink the PEI structure around the protein molecules in an aqueous buffer (pH about 7-10) at the temperature range of 4° C. to room temperature. The final protein nanoparticles encapsulated in the crosslinked PEI-PEG can be further washed on two membrane filters with excessive aqueous buffer (pH optimal for enzyme activity, pH 2-12).

Example 6

Polyethylene Glycol (PEG)/Protein Nanoparticles

Commercially available PEG, functionalized with epoxy or maleic anhydride, can be contacted with protein molecules in an aqueous buffer with a molar excess of PEG over protein (molar ratio ranging from about 10 to about 1000). There will be crosslinking between the amino groups of the protein molecules and epoxy (or maleic anhydride) of PEG, and the crosslinked products in an aqueous buffer can be washed on a first membrane filter having a maximum pore size of 0.1 μm and then on a second membrane filter having a lower MWCO of 10K. This washing procedure will result in the separation of protein-PEG nanoparticles. After excessive washing, a diamine (such as L-lysine or PEI) can be added to induce further crosslinking around the individual protein molecules. This final product can be washed again on two membrane filters (a maximum pore size of 0.1 μm and a lower MWCO of 10K).

Example 7

Siloxane/Protein Nanoparticles

Epoxy-polydimethylsiloxane (PDMS) solubilized in hexane, and protein molecules dissolved in an aqueous buffer solution (pH of about 7-10) may be mixed together. The resulting two-phase system can be shaken to promote a reaction between the epoxy-PDMS and the amino groups of the protein molecules, and extraction of the protein-PDMS product into the hexane phase. The hexane phase containing well-solubilized and hydrated protein-PDMS may be collected, and tetraethyl orthosilicate (TEOS) can be added for silicate formation around the protein molecules. PDMS polymers of various molecular weights can be selected as a spacer for preventing the agglomeration of protein-silicate nanoparticles.

Instead of using epoxy-PDMS, PDMS-PEG can be used for the solubilization of protein in hexane, and TEOS can be added into the separated hexane phase containing hydrated protein-PEG-PDMS. The added TEOS will be hydrolyzed and condensed around each individual protein molecule, and will result in an "armored" shell protecting the individual protein molecules. In this example, there may be no covalent bonds between the protein molecules and the PEG.

What is claimed is:

1. A method for making a biocomposite material, comprising:
   modifying a polypeptide to provide α, β-ethylenically unsaturated functional terminal groups;
   mixing the modified polypeptide with a polymerizable compound that includes (i) a functional group reactive with the α, β-ethylenically unsaturated functional terminal group of the modified polypeptide, and (ii) a silicon-containing functional group;
   subjecting the resulting mixture to conditions sufficient for forming a product that includes biocomposite particles that comprise the polypeptide and a crosslinked polymer shell produced from the polymerizable compound, wherein the crosslinked polymer shell substantially encompasses the polypeptide and is not crosslinked with any other crosslinked polymer shells present in the mixture; and
   isolating a composition from the product, wherein substantially all of the biocomposite particles in the isolated composition each individually do not define a dimension greater than about 1 μm and are not crosslinked together.

2. The method according to claim 1, wherein the polypeptide comprises an enzyme.

3. The method according to claim 1, wherein isolating the composition comprises passing the product through a filter that defines a maximum pore size of 1 μm.

4. The method according to claim 1, wherein substantially all of the biocomposite particles each individually do not define a dimension greater than about 200 nm, and the isolating of the composition comprises passing the product through a filter that defines a maximum pore size of 200 nm.

5. The method according to claim 1, wherein the α, β-ethylenically unsaturated functional terminal groups comprise vinyl groups, and the polymerizable compound comprises a carbon-unsaturated silane compound.

6. The method according to claim 5, wherein the subjecting of the resulting mixture to conditions sufficient for forming a product comprises free radical polymerizing the resulting mixture to produce an intermediate, and then hydrolyzing and condensing the intermediate to produce the product.

7. The method according to claim 6, wherein the hydrolyzing and condensing of the intermediate occurs simultaneously with the isolating of the composition from the product.

8. The method according to claim 7, wherein the hydrolyzing and condensing of the intermediate comprises:
   providing the intermediate in an organic solvent phase;
   mixing the organic solvent phase containing the intermediate with an aqueous buffer solution; and
   extracting the product into the aqueous buffer solution.

9. The method according to claim 8, further comprising passing the extracted aqueous buffer solution through a filter that defines a maximum pore size of 1 μm.

10. The method of claim 5, wherein the polypeptide comprises an enzyme.

11. The method according to claim 1, further comprising passing the modified polypeptide through a filter that defines a maximum pore size of 1 μm, and mixing the modified polypeptide particles in the filtrate with the polymerizable compound.

12. The method according to claim 1, wherein a separate crosslinking agent is not added during the method.

13. The method according to claim 1, wherein substantially all of the biocomposite particles contain a single polypeptide molecule.

14. The method according to claim 1, wherein the method results in a yield of biocomposite particles of about 35% to about 95%, based on the bioactivity of the polypeptide in the biocomposite particle divided by the initial bioactivity of the free polypeptide prior to synthesis of the biocomposite particle.

15. The method according to claim 1, further comprising linking a first modified polypeptide molecule with a second modified polypeptide molecule, wherein the first modified polypeptide molecule and the second modified polypeptide molecule have different polypeptide structures.

16. The method of claim 1, wherein the polymerizable compound has a structure of:

$$R_aSiX_{(4-a)}$$

wherein each R represents an organic moiety that includes at least one carbon-unsaturated bond and in which a carbon atom is bonded directly to the silicon atom, and; a is an integer from 1 to 3; and each X represents at least one moiety selected from a hydroxyl group, an alkoxy group, a siloxy group, an alkyl group, a carboxyl group, or an amino group; and wherein each R moiety may be the same or different and each X moiety may be the same or different.

17. The method of claim 1, wherein modifying a polypeptide to provide α, β-ethylenically unsaturated functional terminal groups comprises reacting the polypeptide with (meth)acrylic acid, (meth)acrylate, substituted (meth)acrylate, or acryloyl chloride.

18. The method of claim 1, wherein the polypeptide is selected from an enzyme, a hormone, a toxin, an antibody, an antigen, a lectin, a structural protein, a signal protein, a transport protein, a receptor, a blood factor, or a mixture thereof.

19. The method of claim 1, wherein the isolating is effected via filtration.

20. The method of claim 1, wherein the biocomposite particles in the isolated composition are provided in a liquid media.

* * * * *